United States Patent [19]

Jarreau, Sr.

[11] 4,055,605

[45] Oct. 25, 1977

[54] PHENOL ALKYLATION

[75] Inventor: Charles L. Jarreau, Sr., Natchez, Miss.

[73] Assignee: Calumet Petrochemicals, Inc., Natchez, Miss.

[21] Appl. No.: 320,265

[22] Filed: Jan. 2, 1973

[51] Int. Cl.² ............................................. C07C 39/06
[52] U.S. Cl. ............................ 260/624 R; 260/626 R; 260/624 C
[58] Field of Search ........... 260/624 R, 624 C, 626 R, 260/626 T, 619 R

[56] References Cited

U.S. PATENT DOCUMENTS

| 2,684,389 | 7/1954 | Offutt | 260/624 C |
| 2,732,408 | 1/1956 | Foote | 260/624 C |

Primary Examiner—James O. Thomas, Jr.
Assistant Examiner—W. B. Lone
Attorney, Agent, or Firm—Vanderveer Voorhees; Thomas A. Schenach

[57] ABSTRACT

Monoalkylphenols are made by passing a mixture of phenol and an olefin of 8–18 carbon atoms through a catalyst bed at 250°–350° F. The catalyst is a granular activated clay and the mol ratio of phenol to olefin charged exceeds 2.0.

2 Claims, 1 Drawing Figure

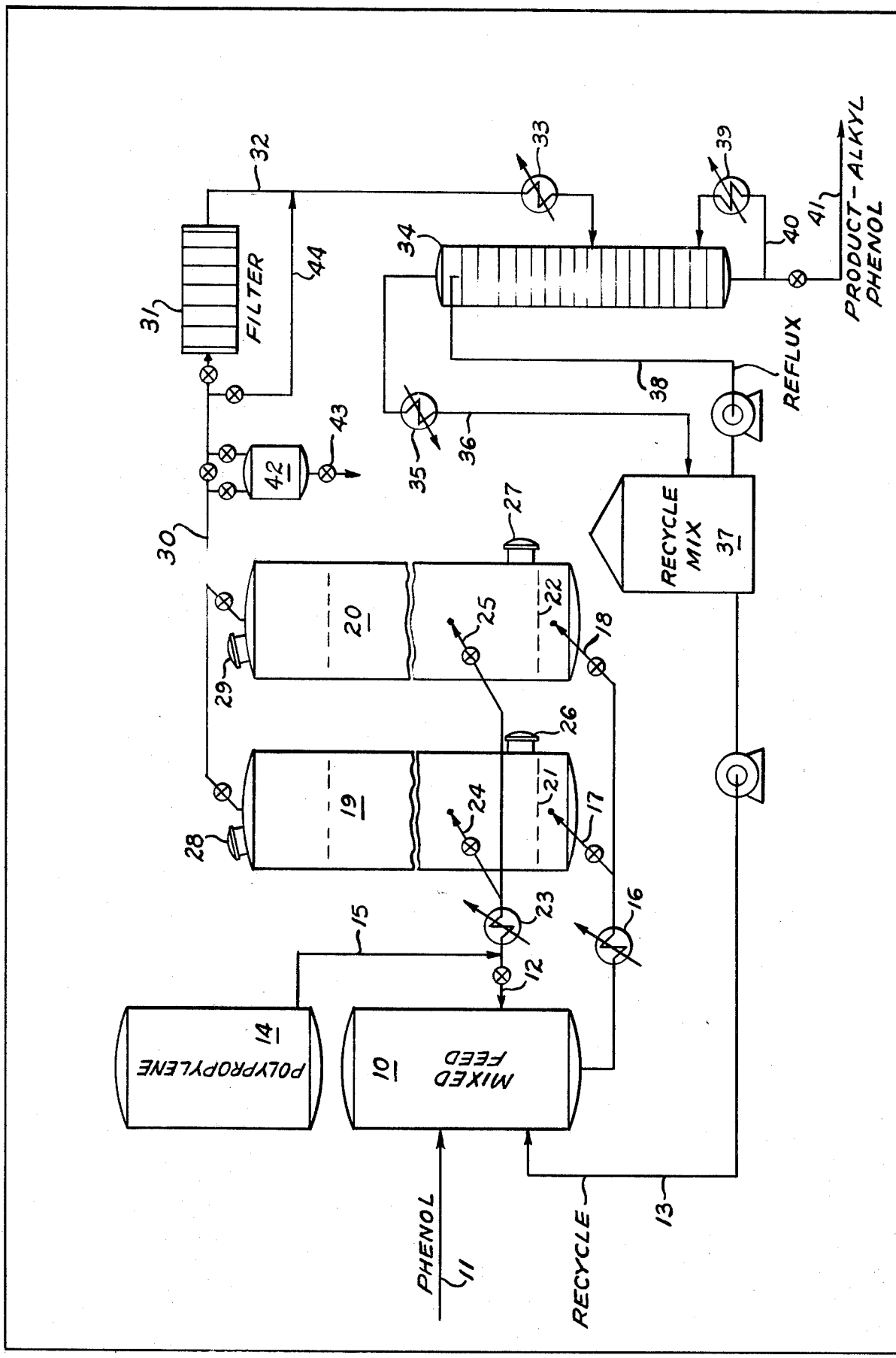

PHENOL ALKYLATION

This invention relates to the manufacture of alkylated phenols and, more particularly, to an improved method of introducing an alkyl group of upwards of 8 carbon atoms into the benzene ring of phenol by the action of an olefin in the presence of a heterogeneous catalyst. The invention relates still more particularly to an alkylation reaction wherein the conditions of the reaction are controlled to give a higher yield of the desired monoalkylphenol than heretofore obtainable. This invention relates also to a simplified process whereby the normal catalyst removal step (filtration) is virtually eliminated, thus greatly reducing the volume of the waste stream normally associated with this process.

The invention is illustrated by a drawing which shows schematically an apparatus suitable for carrying out the process.

One object of the invention is to effect alkylation of phenol, cresol, or xylenol with an olefin having upwards of 8 carbon atoms such as a butylene dimer in a manner to produce an alkylphenol product containing at least 90% monoalkylphenols, the remainder being dialkyl phenols and heavier. Another object of the invention is to alkylate with a heterogeneous catalyst at a higher space velocity than has heretofore been considered possible with heterogeneous catalysts. Another object of the invention is to alkylate phenols with a heterogeneous catalyst and obtain a catalyst life expressed as weight of product per unit weight of catalyst exceeding the catalyst life heretofore obtainable.

The alkylphenols have been known for many years, such as the butyl, amyl and hexyl phenols useful as antiseptics, antioxidants, and starting materials for numerous chemical syntheses. The higher alkylphenols having upwards of 8 carbon atoms in the alkyl group are of more recent development. These are most economically made by condensing an olefin having 8 to 18 carbon atoms with the desired phenol in the presence of a catalyst. Most available olefins in the higher molecular weights range are polymers of propylene and butylene. Polymers of ethylene, the so-called alpha olefins of eight, ten, twelve or more carbon atoms and mixtures thereof, can also be used. The condensation is not difficult and various catalysts can be used, the commonest being Friedel Crafts type, $AlCl_3$, $ZnCl_2$, $BF_3$, and the strong acids, $H_2SO_4$, $H_3PO_4$ and $HF$. These may be generally classed as "homogeneous" catalysts. Acid activated clays can also be used such as acid treated bentonite and montmorillonite. Heretofore, these have usually been used in the form of a fine powder which was added to the mixture of phenol and olefin, heated to effect the reaction, then filtered to recover the catalyst which was either discarded or recycled until its activity was exhausted. Losses of valuable reactants in the spent catalyst were a serious problem with this process.

I have now discovered that such losses can be greatly minimized by the use of a granular catalyst in a fixed bed through which the reactants flow at a controlled rate. The flow may be either upward or downward in a vertical reactor wherein the cross sectional area of the bed is relatively small in relation to the depth, for example, expressing area as diameter, the depth to diameter ratio should be in the range of about 10:1 to 20:1, a suitable bed depth being 20 feet for a diameter (cylindrical tower) or 1.25 feet.

I have found that, owing to the lower activity of my contact catalyst when compared to Friedel Crafts catalysts, I can obtain greater selectivity in the alkylation reaction. Thus, in a typical run, I may have a contact time of 3.5 hours whereas, with aluminum chloride, the reaction would be complete within a few minutes. Accordingly, I can obtain yields of the monoalkylphenol of 95 to 98 percent, making it unnecessary to further purify the product for most purposes. I may re-distill the product in vacuum for some purposes, however, in which case, the color is improved, the product being water white instead of yellow.

I have also found that my catalyst favors the alkylation reaction as opposed to the competing polymerization reaction whereby part of the olefin is polymerized to useless high molecular weight polymers. De-polymerization of olefin polymers such as propylene tetramer, butylene trimer, etc. can also occur with some catalysts such as $AlCl_3$, and even with the activated clays when the temperature is too high. Sulfuric acid and aluminum chloride also have the bad characteristic of rearranging the straight chain olefin to undesirable isomeric structures.

I have found that a temperature in the range of 250° to 350° F. is very effective, the optimum being about 300° F., with a space velocity of about 0.5 to 0.20 volumes per hour per volume of catalyst in the bed, corresponding to a contact time of about 2 to 5 hours. Excellent results were obtained with a contact time of 3.5 hours. In a typical run to a catalyst life of 500 hours, the yield of product under these conditions was 57% per pass, based on the volume of olefin charged-propylene tetramer.

In order to avoid poly alkylation, a high ratio of phenol to olefin should be used, at least 1.5 to 1 on a molar basis and preferably 2–4 mols phenol per mol of olefin. I have discovered that the production of undesired dialkyl phenol can be still further diminished by splitting the olefin feed, charging part of it, e.g. 25 to 50% by volume, to an intermediate point in the catalyst bed. This has the effect of increasing the phenol ratio, inasmuch as the olefin charged at the beginning of the reactor is largely consumed in the alkylation when the stream reaches the intermediate point of the reactor.

Referring now to the drawing:

A mixed feed is prepared in feed tank 10 from phenol charged by line 11 and propylene tetramer ($C_{12}H_{24}$) by line 12. Recycle phenol and tetramer is also charged by line 13. Propylene tetramer enters the system from supply 14 by line 15. From 10 the feed is charged to heater 16 where it is heated to about 300° F., flowing thence by lines 17 and 18 to parallel reactors 19 and 20. These towers are filled with the catalyst in granular form, suitably having a particle size in the range of 15 to 40 mesh. A space above the catalyst bed provides for settling catalyst which may be carried up by the liquid stream. The beds are supported on suitable grids, perforated plates and screens as indicated at 21 and 22. A portion of the olefin feed from line 15 is diverted through heater 23 and lines 24 and 25 to a midpoint in the catalyst beds for the purpose described hereinabove. As the catalyst in each reactor becomes inactive to a degree where it is economically desirable to replace it, it can be removed at the manholes 26 or 27 and recharged at 28 or 29, respectively. By recharging the reactors alternately, it is not necessary to shut down the process.

From reactors 19 and 20, the stream, now containing about 60% by volume of alkylphenol and 40% by volume of unreacted phenol and tetramer, flows by line 30 through filter 31, and line 32 leading through heater 33 into fractionator 34. Here, unreacted phenol and tetramer are removed overhead, condensed in cooler 35 and led by line 36 to recycle mix tank 37. Reflux for fractionator 34 is supplied by line 38. The charge to 34 can be heated in 33 to about 420° F. Additional heat for the lower stripping section of 34 is supplied by heater 39 through which a portion of the bottoms is recycled by line 40. The alkylate product is withdrawn as produced by line 41. Heat from this stream can be transferred to the feed in lines 17 and 18 if desired by the usual exchangers, not shown.

At start-up with a new charge of moist catalyst, water will be driven overhead from the reactors in the form of steam. It is desirable to remove this water from the system by condensing it in trap 42 from which it can be discarded by valve 43. I find it advantageous to dry the catalyst in this manner rather than by a preliminary roast which I find tends to deactivate the catalyst. After steady operating conditions are established and fine particles of catalyst have largely been carried over in the product stream, I can discontinue use of the filter 31, shunting the stream through line 44.

Following are examples of two catalysts manufactured by the Filtrol Corporation which are satisfactory for use in my process:

| Granular Acid Activated Clay | "Filtrol" Grade 24 | "Filtrol" Grade 25 |
|---|---|---|
| Particle Size, Mesh | 20–60 | 10–20 |
| Particle Size Analysis Tyler Standard Sieve | | |
| Through 10 mesh, % | 100 | 100 |
| Through 20 mesh, % | 100 | 5 |
| Through 60 mesh, % | 5 | — |
| Free Moisture, Wt. % | 10 | 10 |
| Free & Combined Moisture, % (loss at 1700° F.) | 15 (max.) | 15 (max.) |
| Bulk Density, lbs./cu. ft. | 47.0 | 43.0 |
| Surface Area ($N_2$ Adsorption) Square meters/gram | 280–300 | 280–300 |
| Acid Number, mgKOH/gram | 15 | 15 |
| Acidity, pH | 3.1 | 3.1 |

The ratio of phenol to olefin—molecular basis—is usually 1.5:1 to 3:1 although a higher ratio, e.g. 4:1, offers the advantage of somewhat lower di-alkyl formation but costs of recycling phenol are increased. A space velocity of 0.3 volumes per volume of catalyst per hour is effective but can be varied from about 0.2 to 0.5 V./V./Hr., depending on temperature and type of olefin employed. Using propylene tetramer, I find the desired monalkylphenol boils in the range of 575° to 630° F. (ASTM-D447). When re-distilling the product under vacuum, the residue of dialkyl phenol can be recycled to the reactor to suppress further production of dialkyl phenol.

After the catalyst has lost a specified amount of activity, e.g. 10%, the reactor 19 or 20, as the case may be, is isolated, liquid is drained from the system, and the catalyst is extracted with a suitable solvent before discarding it. Because of the high yield of product obtained in my process, it is not economically necessary to attempt to recover the spent catalyst. Solvents which can be used to recover reactants are benzene, water, glycol monomethyl ether, etc.

Inasmuch as the alkylation reaction is slightly exothermic, cooling coils can be installed in the reactors 19 and 20 to control the temperature, but I find that recycling phenol in the process serves to absorb heat of reaction and stabilize the temperature, making cooling unnecessary.

The following examples illustrate the reaction between phenol, $C_6H_5OH$, and propylene tetramer—dodecene, $C_{12}H_{24}$. The phenol had a boiling point of 359° F. and a density of 1.057 equal to 8.826 pounds per gallon. The tetramer had a boiling range of 350° F. initial to 380° F. final and a density of 6.46 pounds per gallon at 60° F.

EXAMPLE 1

A pilot plant (semi works) was designed with a reaction vessel consisting of a cylindrical tower 30 feet in height and 16 inches diameter. A heating coil in the base served to preheat the charge to the desired reaction temperature, in this case, 300° F. Above the coil is placed the catalyst in a bed 20 feet in depth, in this case, activated clay known as "Filtrol 25", the volume of catalyst being 235 gallons.

To the reactor, at the bottom is charged a mixture of propylene tetramer, phenol and recycle in the following proportions:

| | |
|---|---|
| Tetramer | 0.39 gal. per minute |
| New Phenol | 0.144 gal. per minute |
| Recycle Phenol | 0.5 gal. per minute |
| Total Phenol Charged | 0.644 gal. per minute |
| Mol Ratio Phenol/Tetramer Charged | 1.8 |
| Total Flow-thru Reactor | 60 gal. per hour |
| Space Velocity | 0.255 V./V./Hr. at 60° F. |
| | 0.294 V./V./Hr. at 300° F. |

From the reactor, the stream passes to a vacuum still where unreacted phenol and tetramer is removed overhead at the rate of 0.45 gallons per minute to be recycled to the reactor. Alkyl phenol product is withdrawn as a residue from the still at the rate of 0.55 gallons per minute, cooled and sent to storage. Recycle phenol contains about 40% by volume of tetramer unreacted and available for further conversion in the next pass through the catalyst. The yield of product is about 87% based on the fresh charge of phenol and tetramer and comprises about 94.5% of monoalkylphenol by weight and 5.5% dialkyl phenol. This amount of dialkyl phenol is generally acceptable for many purposes such as the manufacture of calcium phenates and thiophosphates employed as lubricating oil additives.

In one run in which the catalyst was used for a period of 1,020 hours, there was obtained a yield of alkylate product of 158 gallons per gallon of catalyst used in the reactor or 372,000 pounds per ton of catalyst, resulting in a catalyst cost of only 4.46 mils per pound based on a catalyst cost of $167.50 per net ton.

EXAMPLE 2

The following results were obtained with a catalyst which had been in service for a period of 350 hours at about 300° F.

| | Fresh | Recycle | Total |
|---|---|---|---|
| Phenol charge, c.c./min. | 11.7 | — | 11.7 (0.128 Mols) |
| Tetramer charge, c.c./min. | 12.0 | — | 12.0 (0.054 Mols) |
| Total Flow | | | 23.2 c.c./min. |
| Mol Ratio, Phenol/Tetramer | | | 2.34 |
| Contact Time | | | 3.31 hours |
| Space Velocity, V./V./Hr. | | | 0.302 |
| Temperature of Catalyst Bed, ° F. | | | 301 |
| Yield of Alkylphenol Product, % by volume, Total Charge | | | 63 |
| Specific Gravity of Crude | | | |

-continued

| | Fresh | Recycle | Total |
|---|---|---|---|
| Undistilled product | | | 0.9510 |
| Initial Boiling Point. ° | 324 | | |
| Color, ASTM Saybolt | | | 3.5 |
| Specific Gravity of Product | | | 0.935 |
| ASTM D-447 Distillation Data: | | | |
| IBP | | 324 | |
| 5% | | 338 | |
| 10% | | 347 | |
| 15 | | 350 | |
| 20 | | 363 | |
| 25 | | 380 | |
| 30 | | 385 | |
| 35 | | 500 | |
| 40 | | 594 | |
| 45 | | 600 | |
| 50 | | 602 | |
| 55 | | 608 | |
| 60 | | 611 | |
| 65 | | 611 | |
| 70 | | 616 | |
| 75 | | 618 | |
| 80 | | 620 | |
| 85 | | 627 | |
| 90 | | 642 | |
| 95% | | 652 | |
| E.P. | | 652 | |

Having thus described my invention, what I claim is:

1. In the process of preparing monoalkylphenols wherein an olefin hydrocarbon having from 8 to 18 carbon atoms is reacted with a phenol selected from the group consisting of phenol, cresol, and xylenol in the presence of a catalyst consisting essentially of an acid activated clay, the improvement comprising passing a stream of the liquid mixture of phenol and olefin through a stationary bed of activated clay catalyst in granular form in a vertically elongated reaction zone at a rate corresponding to a space velocity of 0.2 to 0.5 volumes per volume of catalyst per hour and a temperature of 250° to 350° F., a portion of the olefin charged to said reaction zone being introduced thereinto at an intermediate point therein, thereby increasing further the average mol ratio of phenol to olefin in said catalyst bed, said catalyst having an acid value of about 12-15, and acidity of about 3-3.4 pH, and a particle size of about 15 to 40 mesh, maintaining an excess of phenol in said catalyst bed corresponding to a mol ratio of about 1.5 to 3.5, distilling unreacted phenol from the stream leaving the catalyst and recycling said recovered phenol to said reaction zone.

2. In the process of preparing monoalkylphenols wherein an olefin hydrocarbon having from 8 to 18 carbon atoms is reacted with a phenol selected from the group consisting of phenol, cresol, and xylenol in the presence of a catalyst consisting essentially of an acid activated clay, the improvement comprising passing a stream of the liquid mixture of phenol and olefin through a stationary bed of activated clay catalyst in granular form in a vertically elongated reaction zone at a rate corresponding to a space velocity of 0.2 to 0.5 volumes per volume of catalyst per hour and a temperature of 250° to 350° F., said catalyst having an acid value of about 12-15, an acidity of about 3-3.4 pH, and a particle size of about 15 to 40 mesh, maintaining an excess of phenol in said catalyst bed corresponding to a mol ratio of about 1.5 to 3.5, distilling unreacted phenol from the stream leaving the catalyst and recyling said recovered phenol to said reaction zone, further distilling to provide a monoalkylphenol distillate and a residue consisting principally of dialkyl phenol, and recycling said dialkyl phenol to the said reaction zone to suppress formation of further amounts of dialkyl phenol therein.

* * * * *